US008507645B2

(12) United States Patent
Funk et al.

(10) Patent No.: US 8,507,645 B2
(45) Date of Patent: Aug. 13, 2013

(54) PROCESS FOR CONTINUOUSLY PRODUCING WATER-ABSORBING POLYMER PARTICLES

(75) Inventors: Rüdiger Funk, Niedernhausen (DE); Thomas Pfeiffer, Boehl-Iggelheim (DE); Karl J. Possemiers, Gravenwezel (BE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/478,423

(22) Filed: May 23, 2012

(65) Prior Publication Data

US 2012/0302711 A1    Nov. 29, 2012

Related U.S. Application Data

(60) Provisional application No. 61/490,084, filed on May 26, 2011.

(51) Int. Cl.
*C08F 6/00* (2006.01)
*C08F 63/02* (2006.01)
(52) U.S. Cl.
USPC .......................................... 528/502

(58) Field of Classification Search
USPC .................................. 528/204, 502
See application file for complete search history.

(56) References Cited

U.S. PATENT DOCUMENTS

2012/0283401 A1* 11/2012 Funk et al. ............... 526/181

FOREIGN PATENT DOCUMENTS

EP        1 418 000 A2    5/2004
WO    WO-03/051415 A1    6/2003

OTHER PUBLICATIONS

Buchholz, Fredric L., et al. *Modern Superabsorbent Polymer Technology*, "Solution Polymerization: Unit Operations and Their Effect on Product Quality." New York: John Wiley & Sons, Inc., 1998, pp. 71-103.

* cited by examiner

*Primary Examiner* — Terressa Boykin
(74) *Attorney, Agent, or Firm* — Marshall, Gerstein & Borun LLP

(57) ABSTRACT

A process for continuously producing water-absorbing polymer particles, in a continuous polymerization reactor, wherein the amount of initiator used and/or the intensity of the UV radiation optionally used to initiate the polymerization is reduced after the startup of the polymerization reactor.

10 Claims, No Drawings

PROCESS FOR CONTINUOUSLY PRODUCING WATER-ABSORBING POLYMER PARTICLES

CROSS-REFERENCE TO RELATED APPLICATIONS

This application claims the benefit of U.S. Provisional Patent Application No. 61/490,084, filed May 26, 2011, incorporated herein by reference in its entirety.

The present invention relates to a process for continuously producing water-absorbing polymer particles in a continuous polymerization reactor, wherein the amount of initiator used and/or the intensity of the UV radiation used to initiate the polymerization is reduced after the startup of the polymerization reactor.

Water-absorbing polymers are used to produce diapers, tampons, sanitary napkins and other hygiene articles, but also as water-retaining agents in market gardening. The water-absorbing polymer particles are also referred to as superabsorbents.

The production of water-absorbing polymer particles is described, for example, in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the performance properties, for example permeability of the swollen gel bed (SFC) in the diaper and absorption under a pressure of 49.2 g/cm$^2$ (AUL0.7 psi), water-absorbing polymer particles are generally surface postcrosslinked. This increases the degree of crosslinking of the particle surface, which allows the absorption under a pressure of 49.2 g/cm$^2$ (AUL0.7 psi) and the centrifuge retention capacity (CRC) to be at least partially decoupled. This surface postcrosslinking can be carried out in the aqueous gel phase. However, preference is given to surface coating dried, ground and sieved-off polymer particles (base polymer) with a surface postcrosslinker and thermally surface postcrosslinking them. Crosslinkers suitable for this purpose are compounds which can form covalent bonds with at least two carboxylate groups of the water-absorbing polymer particles.

WO 03/051415 A1 describes continuous production of water-absorbing polymer particles in a kneading reactor, wherein the monomer solution used has a temperature of at least 40° C.

EP 1 418 000 A2 discloses continuous production of water-absorbing polymer particles in a belt reactor, wherein a heated monomer solution is likewise used.

It was an object of the present invention to provide an improved process for producing water-absorbing polymer particles, more particularly with a high centrifuge retention capacity (CRC) and a low level of extractables.

The object was achieved by a process for producing water-absorbing polymer particles by polymerizing a monomer solution or suspension comprising a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers specified under a) and
e) optionally one or more water-soluble polymers, in a continuous polymerization reactor to give a polymer gel, drying the resulting polymer gel, comminuting the dry polymer gel to give polymer particles and classifying the resulting polymer particles, wherein the amount of initiator c) used and/or the intensity of the UV radiation optionally used to initiate the polymerization are lowered by at least 10% within the first 120 minutes after the startup of the polymerization reactor.

The amount of initiator c) used and/or the intensity of the UV radiation optionally used for initiation of the polymerization is preferably lowered by preferably at least 20%, more preferably at least 30%, most preferably at least 40%, within the first 90 minutes, more preferably within the first 60 minutes, most preferably within the first 30 minutes, after the startup of the polymerization reactor.

It is typically unnecessary to again raise the amount of initiator c) used and/or to increase the intensity of the UV radiation optionally used for initiation of the polymerization during the continuous operation of the polymerization reactor, except as a reaction to any disruption which occurs.

The present invention is based on the finding that, on startup of a continuous polymerization reactor for production of water-absorbing polymer particles, stronger initiation is needed than in the course of later continuous operation. Therefore, the initiation can be reduced a certain time after the startup of the polymerization reactor. It is also possible to reduce the initiation stepwise.

For simplification, the initiation on startup, irrespective of the formulation used in continuous operation, can be fixed at a high value suitable for all formulations.

As a result of the higher initiation in the course of startup, the polymerization can be initiated faster and a steady state is attained faster. This is necessary since the monomer solution at the beginning can flow freely from one end to the other end of the polymerization zone and thus some of the reaction mixture has only an inadequate residence time in the reaction zone.

In the case of brief interruptions in which the polymerization reactor has not been emptied, the startup procedure can be shortened correspondingly. In the case of longer interruptions, the polymerization reactor and the feed lines are emptied. To avoid polymer coking during shutdown, the feed lines of the monomer solution are emptied and purged. Suitable substances for purging are nitrogen, air and/or demineralized water.

The mean residence time in the polymerization reactor is preferably 5 to 120 minutes, more preferably 10 to 90 minutes, most preferably 15 to 60 minutes.

On startup, the polymerization reactor is preferably operated at 40 to 80%, more preferably 50 to 75%, most preferably 60 to 70%, of the nominal load, the nominal load being the quantitative feed of monomer solution in steady-state operation.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

The kneader reactors usable with preference in the process according to the invention have at least two shafts which rotate in an axially parallel manner, several kneading and transport elements typically being present on the shafts.

Prior to startup, the polymerization reactor is preheated to a temperature of 30 to 120° C., more preferably 60 to 100° C., most preferably 80 to 90° C.

In the case of a kneading reactor, the preheating is effected preferably by means of a trace-heated jacket. Suitable heat carriers are hot water and steam. Preference is given here to steam since the temperature of the steam can be adjusted in a very simple manner via the pressure. This can be accomplished, for example, by decompressing relatively high-pressure steam with subsequent saturation of the superheated water vapor thus obtained.

The steam has a pressure of preferably 1.4 to 16 bar, more preferably of 1.8 to 11 bar, most preferably of 2 to 4 bar.

Suitable kneading reactors are obtainable, for example, from List AG (Arisdorf; Switzerland) and are described in CH 664 704 A5, EP 0 517 068 A1, WO 97/12666 A1, DE 21 23 956 A1, EP 0 603 525 A1, DE 195 36 944 A1 and DE 41 18 884 A1.

Such kneading reactors with at least two shafts achieve, through the arrangement of the kneading and transport elements, a high level of self-cleaning, which is an important requirement for a continuous polymerization. The two shafts preferably rotate counter to one another.

On the stirrer shaft, the disk segments are arranged in the manner of a propeller. Suitable kneading transport elements are, for example, close-clearance mixing bars and L- or U-shaped protrusions.

The production of the water-absorbing polymer particles is explained in detail hereinafter:

The water-absorbing polymer particles are prepared by polymerizing a monomer solution or suspension and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions containing excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

To improve the drying properties, the comminuted polymer gel obtained by means of a kneading reactor can additionally be extruded.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 95 mol %, more preferably from 30 to 80 mol %, most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably from 0.5 to 15% by weight, more preferably from 1 to 10% by weight, most preferably from 2 to 8% by weight, the residual moisture content being determined by the EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of the EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of greater than 150 µm is preferably at least 90% by weight, more preferably at least 95% by weight, most preferably at least 98% by weight.

Polymer particles with too small a particle size lower the permeability (SFC). The proportion of excessively small polymer particles ("fines") should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated for, for example, by adjusting the amount of crosslinker b) used.

When the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

The proportion of particles having a particle size of at most 600 μm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 83 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and its derivatives, such as 2-hydroxyethyl-2-oxazolidinone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and its derivatives in WO 2003/31482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably from 0.001 to 2% by weight, more preferably from 0.02 to 1% by weight, most preferably from 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts, such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, from 0.001 to 1.5% by weight, preferably from 0.005 to 1% by weight, more preferably from 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio is preferably from 20:80 to 40:60.

The thermal drying is preferably carried out in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany), Holo-Flite® dryers (Metso Minerals Industries Inc.; Danville; USA) and Nara Paddle Dryer (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range from 100 to 250° C., preferably from 120 to 220° C., more preferably from 130 to 210° C., most preferably from 150 to 200° C. The preferred residence time at this temperature in the reaction mixer or drier is preferably at least 10 minutes, more preferably at least 20 minutes, most preferably at least 30 minutes, and typically at most 60 minutes.

In a preferred embodiment of the present invention, the water-absorbing polymer particles are cooled after the thermal drying. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disc Cooler (Hosokawa Micron GmbH; Leingarten; Germany), Holo-Flite® coolers (Metso Minerals Industries Inc.; Danville; USA) and Nara Paddle Cooler (NARA Machinery Europe; Frechen; Germany). Moreover, fluidized bed coolers may also be used.

In the cooler, the water-absorbing polymer particles are cooled to 20 to 150° C., preferably 30 to 120° C., more preferably 40 to 100° C. and most preferably 50 to 80° C.

Subsequently, the surface postcrosslinked polymer particles can be classified again, excessively small and/or excessively large polymer particles being removed and recycled into the process.

To further improve the properties, the surface postcrosslinked polymer particles can be coated or subsequently moistened. The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging. The remoisturizing is advantageously performed in the cooler after the thermal drying.

Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles produced by the process according to the invention have a moisture content of preferably from 0 to 15% by weight, more preferably from 0.2 to 10% by weight, most preferably from 0.5 to 8% by weight, the moisture content being determined by the EDANA recommended test method No. WSP 230.2-05 "Mass Loss Upon Heating".

The water-absorbing polymer particles produced by the process according to the invention have a proportion of particles with a particle size of 300 to 600 μm of preferably at least 30% by weight, more preferably at least 50% by weight, most preferably at least 70% by weight.

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by the EDANA recommended test method No. WSP 241.2-05 "Fluid Retention Capacity in Saline, After Centrifugation".

The water-absorbing polymer particles produced by the process according to the invention have an absorption under a pressure of 49.2 g/cm$^2$ of typically at least 15 g/g, preferably at least 20 g/g, preferentially at least 22 g/g, more preferably at least 24 g/g, most preferably at least 26 g/g. The absorption under a pressure of 49.2 g/cm$^2$ of the water-absorbing polymer particles is typically less than 35 g/g. The absorption under a pressure of 49.2 g/cm$^2$ is determined analogously to the EDANA recommended test method No. WSP 242.2-05 "Absorption Under Pressure, Gravimetric Determination", except that a pressure of 49.2 g/cm$^2$ is established instead of a pressure of 21.0 g/cm$^2$.

METHODS

The standard test methods described hereinafter and designated "WSP" are described in: "Standard Test Methods for the Nonwovens Industry", 2005 edition, published jointly by the Worldwide Strategic Partners EDANA (Avenue Eugene Plasky, 157, 1030 Brussels, Belgium, www.edana.org) and INDA (1100 Crescent Green, Suite 115, Cary, N.C. 27518, U.S.A., www.inda.org). This publication is available both from EDANA and from INDA.

The analyses should, unless stated otherwise, be performed at an ambient temperature of 23±2° C. and a relative air humidity of 50±10%. The water-absorbing polymer particles are mixed thoroughly before the analysis.

Centrifuge Retention Capacity

The centrifuge retention capacity (CRC) is determined by the EDANA recommended test method No. WSP 241.2-05 "Fluid Retention Capacity in Saline, After Centrifugation".

Extractables

The content of extractable constituents in the water-absorbing polymer particles is determined by the EDANA recommended test method No. WSP 270.2-05 "Extractable".

EXAMPLES

Example 1

A solution, cooled to approx. 15° C., of 75.7 g of acrylic acid, 681.7 g of aqueous sodium acrylate solution (37.3% strength by weight), 235.3 g of deionized water and 1.35 g of 3-tuply ethoxylated glyceryl triacrylate (approx. 85% strength by weight) was freed of atmospheric oxygen by introducing nitrogen for 30 minutes. The polymerization was initiated in a 2 liter plastic vessel by adding 3.0 g of aqueous sodium peroxodisulfate solution (25.2% strength by weight), 4.0 g of aqueous ascorbic acid solution (0.40% strength by weight) and 5.0 g of aqueous hydrogen peroxide solution (0.08% strength by weight). The resulting gel was comminuted with a meat grinder and then dried in a forced air drying cabinet at 150° C. for 60 minutes, ground with a roll mill and adjusted to a particle size range of 150 μm to 850 μm by sieving.

The resulting polymer particles were analyzed. The results are compiled in table 1.

Example 2

The procedure was as in Example 1. The amounts of each of sodium peroxodisulfate, ascorbic acid and hydrogen peroxide was halved. The polymer particles obtained were analyzed. The results are compiled in table 1.

TABLE 1

| | Examples 1 and 2 | |
|---|---|---|
| | CRC [g/g] | Extractables [% by weight] |
| Ex. 1 | 35.2 | 10.3 |
| Ex. 2 (½ amount of initiator) | 36.5 | 8.6 |

Example 3

A solution, cooled to approx. 15° C., of 105.1 g of acrylic acid, 683.3 g of aqueous sodium acrylate solution (37.3% strength by weight), 204.1 g of deionized water and 1.50 g of 3-tuply ethoxylated glyceryl triacrylate (approx. 85% strength by weight) was freed of atmospheric oxygen by introducing nitrogen for 30 minutes. The polymerization was initiated in a 2 liter plastic vessel by adding 3.0 g of aqueous sodium persulfate solution (28.0% strength by weight), 2.0 g of aqueous ascorbic acid solution (0.46% strength by weight) and 5.0 g of aqueous hydrogen peroxide solution (0.1% strength by weight). The reaction mixture reached a temperature of 100° C. after 12 minutes. The resulting gel was comminuted with a meat grinder and then dried in a forced air drying cabinet at 150° C. for 60 minutes, ground with a roll mill and adjusted to a particle size range of 150 μm to 850 μm by sieving.

The resulting polymer particles were analyzed. The results are compiled in table 2.

Example 4

The procedure was as in Example 3. The amounts of each of sodium peroxodisulfate, ascorbic acid and hydrogen peroxide was halved. The reaction mixture reached a temperature of 100° C. after 18 minutes. The resulting polymer particles were analyzed. The results are compiled in table 2.

TABLE 2

| | Examples 3 and 4 | |
|---|---|---|
| | CRC [g/g] | Extractables [% by weight] |
| Ex. 3 | 31.1 | 12.2 |
| Ex. 4 (½ amount of initiator) | 32.3 | 11.2 |

Example 5

A solution, cooled to approx. 15° C., of 39.0 g of acrylic acid, 349.1 g of aqueous sodium acrylate solution (37.3% strength by weight), 105.2 g of deionized water and 0.70 g of 3-tuply ethoxylated glyceryl triacrylate (approx. 85% strength by weight) was freed of atmospheric oxygen by introducing nitrogen for 30 minutes. The polymerization was initiated in a 1 liter glass vessel by adding 3.0 g of aqueous sodium persulfate solution (20.0% strength by weight), 1.5 g of aqueous ascorbic acid solution (0.84% strength by weight) and 1.5 g of aqueous hydrogen peroxide solution (0.74% strength by weight). The resulting gel was comminuted with a meat grinder and then dried in a forced air drying cabinet at 150° C. for 60 minutes, ground with a roll mill and adjusted to a particle size range of 150 μm to 850 μm by sieving.

The resulting polymer particles were analyzed. The results are compiled in table 3.

Example 6

Example 5 was repeated. The results are compiled in table 3.

Example 7

The procedure was as in Example 5. The amounts of each of sodium peroxodisulfate, ascorbic acid and hydrogen peroxide were lowered to two thirds. The resulting polymer particles were analyzed. The results are compiled in table 3.

Example 8

Example 7 was repeated. The results are compiled in table 3.

Example 9

The procedure was as in Example 5. The amounts of sodium peroxodisulfate, ascorbic acid and hydrogen peroxide were each lowered to one third. The resulting polymer particles were analyzed. The results are compiled in table 3.

Example 10

Example 9 was repeated. The resulting product could not be ground.

TABLE 3

| | Examples 5 to 10 | |
|---|---|---|
| | CRC [g/g] | Extractables [% by weight] |
| Ex. 5 | 32.5 | 16.9 |
| Ex. 6 | 32.8 | 18.5 |
| Ex. 7 (⅔ amount of initiator) | 34.1 | 13.7 |
| Ex. 8 (⅔ amount of initiator) | 34.4 | 15.1 |
| Ex. 9 (⅓ amount of initiator) | 50.9 | 55.8 |
| Ex. 10 (⅓ amount of initiator) | — | — |

The results show the influence of the initiation on the product quality. The lowering of the initiation needed on startup in continuous operation thus leads to a distinct improvement.

The invention claimed is:

1. A process for continuously producing water-absorbing polymer particles by polymerizing a monomer solution or suspension comprising
   a) at least one ethylenically unsaturated monomer which bears an acid group and may be at least partly neutralized,
   b) at least one crosslinker,
   c) at least one initiator,
   d) optionally one or more ethylenically unsaturated monomers copolymerizable with the monomers specified under a), and
   e) optionally one or more water-soluble polymers,
in a continuous polymerization reactor to give a polymer gel, drying the resulting polymer gel, comminuting the dry polymer gel to give polymer particles and classifying the resulting polymer particles, wherein the amount of initiator c) used and/or the intensity of the UV radiation optionally used to initiate the polymerization are lowered by at least 10% within first 120 minutes after startup of the polymerization reactor.

2. The process according to claim 1, wherein the amount of initiator c) used is lowered by at least 40% within the first 30 minutes after the startup of the polymerization reactor.

3. The process according to claim 1, wherein the polymerization reactor is preheated to at least 50° C. before the startup of the polymerization.

4. The process according to claim 1, wherein a mean residence time in the polymerization reactor is from 5 to 120 minutes.

5. The process according to claim 1, wherein the polymerization reactor is a kneading reactor.

6. The process according to claim 1, wherein the polymerization reactor is a belt reactor.

7. The process according to claim 1, wherein the water-absorbing polymer particles are surface postcrosslinked, optionally coated, and optionally classified.

8. The process according to claim 1, wherein the monomer a) is acrylic acid partly neutralized to an extent of at least 50 mol %.

9. The process according to claim 1, wherein the monomer a) has been neutralized to an extent of 25 to 85 mol %.

10. The process according to claim 1, wherein the water-absorbing polymer particles have a centrifuge retention capacity of at least 15 g/g.

* * * * *